US00PP10303P

United States Patent [19]

Kientzler

[11] Patent Number: Plant 10,303

[45] Date of Patent: Mar. 24, 1998

[54] NEW GUINEA IMPATIENS PLANT NAMED 'LOPINGA'

[75] Inventor: Ludwig Kientzler, Gensingen, Germany

[73] Assignee: Paul Ecke Ranch, Inc., Encinitas, Calif.

[21] Appl. No.: 778,881

[22] Filed: Jan. 3, 1997

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Lopinga', characterized by its large flat and rounded dark salmon to light red-colored flowers with a white "eye"; freely flowering habit; compact, upright to outwardly spreading growth habit; freely branching plant habit; and dark green, somewhat glossy, non-variegated foliage.

1 Drawing Sheet

The present invention relates to a new and distinct cultivar of New Guinea Impatiens plant, botanically known as *Impatiens hawkeri*, known by the name Kilop, and hereinafter referred to by the cultivar name Lopinga.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as S455 as the male, or pollen parent, with the proprietary seedling selection identified as W928 as the female, or seed patent. The cultivar Lopinga was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Lopinga'. These characteristics in combination distinguish 'Lopinga' as a new and distinct cultivar:

1. Large flat and rounded dark salmon to light red-colored flowers with a white "eye".
2. Freely flowering habit.
3. Compact, upright to outwardly spreading growth habit.
4. Dark green, somewhat glossy, non-variegated foliage.

The new New Guinea Impatiens is similar in flower color to the New Guinea Impatiens cultivar 'BSR-5 Salmon' (disclosed in U.S. Plant Pat. No. 8,870). However in side-by-side comparisons in Encinitas, Calif., under commercial practice, plants of the new New Guinea Impatiens differed from plants of the cultivar 'BSR-195 Salmon' in the following characteristics:

1. Plants of the new New Guinea Impatiens more outwardly spreading and mounded than plants of the cultivar 'BSR-195 Salmon'.
2. Plants of the new New Guinea Impatiens are more freely branching than plants of the cultivar 'BSR-195 Salmon'.
3. Stems of plants of the new New Gninea Impatiens have longer internodes than stems of plants of the cultivar 'BSR-195 Salmon'.
4. Stems of plants of the new New Guinea Impatiens are dark red whereas stems of plants of the cultivar 'BSR-195 Salmon' are green.

5. Leaves of plants of the new New Guinea Impatiens are not variegated however leaves of plants of the cultivar 'BSR-195 Salmon' have a yellow variegation pattern.
6. Leaves of the new New Guinea Impatiens are not as glossy as leaves of plants of the cultivar 'BSR-195 Salmon'.
7. Flowers of plants of the new New Guinea Impatiens are rounded whereas flowers of plants of the cultivar 'BSR-195 Salmon' are star-shaped.
8. Flowers of plants of the new New Guinea Impatiens have a white "eye" whereas flowers of plants of the cultivar 'BSR-195 Salmon' are solid in color.

A detailed comparison of plants of the new New Guinea Impatiens and the cultivar 'BSR-195 Salmon' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Lopinga'.

The second photograph comprises a close-up view of typical flowers and upper (left) and lower (right) surfaces of leaves of the cultivars 'BSR-195 Salmon' (top of photo) and 'Lopinga' (bottom of photo).

Flower and foliage colors in the photographs may differ from the actual colors due to light reflectance.

The cultivar Lopinga has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif., under commercial practice in a fiberglass-covered greenhouse with day temperatures ranging from 23 to 29C and night temperatures ranging from 16 to 18C and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* 'Lopinga'.

*Commercial.*—New Guinea Impatiens cv. 'Lopinga'.

Parentage:

*Male parent.*—Proprietary seeding selection S455.

*Female parent.*—Proprietary seedling selection W928.

Propagaton:

*Type cutting.*—Terminal cuttings.

*Time to initiate roots.*—About 15 days with 21C soil temperature.

Plant description:

*Plant form.*—Compact, upright to outwardly spreading and mounded.

*Growth habit.*—Moderately vigorous. Moderate branching, dense and bushy. Suitable for 10 to 25-cm containers.

*Plant size.*—Height: About 13 cm. Width or spread: About 24 cm.

*Lateral branches.*—Quantity: Six to seven. Size: Length: About 11 cm. Diameter: About 1 cm. Internode length: About 5 cm. Color: 59A.

*Foliage description.*—Leaves simple, generally symmetrical, abundant, opposite or in whorls of three, horizontal to plant and flat in aspect. Size, largest leaves: Length: About 10 cm. Width: About 4 cm. Shape: Ovate with acuminate apex, attenuate base and ciliate margin. Texture: Smooth, somewhat glossy. Color: Young foliage, upper surface: 146A. Young foliage, lower surface: 146B. Fully expanded foliage, upper surface: 147A. Fully expanded foliage, lower surface: 147B. Venation, upper surface: 59A. Venation, lower surface: 59A. Petiole: Size: Length: About 2.25 cm. Diameter: About 3.5 mm. Color: 59A.

Flower description:

*Flower type and habit.*—Large dark salmon to light red-colored flowers. Freely and continuously flowering. Flowers arise from leaf axils. Usually ten flowers per lateral branch. Flowers positioned at or above the foliage and face outward. Flowers flat and rounded. Flowers persistent.

*Flowering season.*—Year-round under greenhouse conditions. In the garden, flowering is continuous from spring until fall.

*Flower size.*—Length: About 7.5 cm. Width: About 6.5 cm. Depth: About 6 mm.

*Flower buds.*—Size: Length: About 1.8 cm. Diameter: About 1.1 cm. Shape: Ovoid. Color: 40C.

*Petals.*—Quantity: Five. Size (largest petals): Length: Top petal: About 3 cm. Middle petals: About 3 cm. Bottom petals: About 3 cm. Width: Top petal: About 5 cm. Middle petals: About 2.5 cm. Bottom petals: About 4 cm. Shape: Cordate with emarginate apex, cuneate or obtuse base and entire margin. Texture: Smooth. Color: When opening, upper surface: Iridescent, slightly brighter than 46C. When opening, lower surface: Iridescent, 46D. Fully opened, upper surface: Iridescent, 46C to brighter than 50A with white at base forming a white "eye". Fully opened, lower surface: Iridescent, 47C with white at base. Fading to: Color does not fade.

*Spur.*—Length: About 5 cm. Shape: Narrow and curved. Color: 53A.

*Peduncles.*—Length: About 4 cm. Angle: Mostly outward. Strength: Strong. Color: 53A.

*Reproductive organs.*—Androecium: Stamen number: Five, anthers fused, filaments free. Anther shape: Obovate. Anther size: 6 by 4 mm. Anther color: Very light yellow. Filament color: 45A. Amount of pollen: Moderate. Pollen color: Cream. Gynoecium: Five-loculate fused. Stigma color: White. Gynoecium color: 144A to 59A.

Disease resistance: Under commercial conditions, resistance nor susceptibility to pathogens has not been observed.

Seed development. Seed production is not usually observed.

CHART A

| CHARACTERISTIC | 'LOPINGA' | 'BSR-195 SALMON' |
|---|---|---|
| GROWTH HABIT | upright to outwardly spreading, mounded | Upright, open form |
| NUMBER OF LATERAL BRANCHES | 6 to 7 | About 5 |
| LATERAL BRANCH LENGTH | About 11 cm | About 13 cm |
| LATERAL BRANCH DIAMETER | About 1 cm | About 8 mm |
| INTERNODE LENGTH | About 5 cm | 2 to 3 cm |
| STEM COLOR | 59A | 144A |
| LEAF LENGTH | About 10 cm | About 11 cm |
| LEAF WIDTH | About 4 cm | About 5.5 cm |
| LEAF VARIEGATION | None | Yellow variegation on mature leaves |
| LEAF VENATION COLOR, UPPER SURFACE | 59A | 148B with slight reddish tinge |
| LEAF VENATION COLOR, LOWER SURFACE | 59A | 147C |
| LEAF TEXTURE | Smooth, somewhat glossy | Glossy |
| PETIOLE LENGTH | About 2.25 cm | About 4.5 cm |
| PETIOLE COLOR | 59A | Light green to red |
| SPUR LENGTH | About 5 cm | About 6 cm |
| SPUR COLOR | 53A | 59A |
| FLOWER BUD COLOR | 40C | 46C |
| PEDUNCLE COLOR | 53A | 145B |
| FLOWER SHAPE | Rounded | Star-shaped |
| PETAL COLOR, WHEN OPENING, UPPER SURFACE | Slightly brighter than 46C | 44B |
| PETAL COLOR, WHEN OPENING, LOWER SURFACE | 46D | 44D |
| PETAL COLOR, OPENED, UPPER SURFACE | 46C to brighter than 50A with white at base forming a white "eye" | 44B, no white "eye" |
| PETAL COLOR, OPENED, LOWER SURFACE | 47C with white at base | 44D |

It is claimed:

1. A new and distinct cultivar of New Guinea Impatiens plant named 'Lopinga', as illustrated and described.

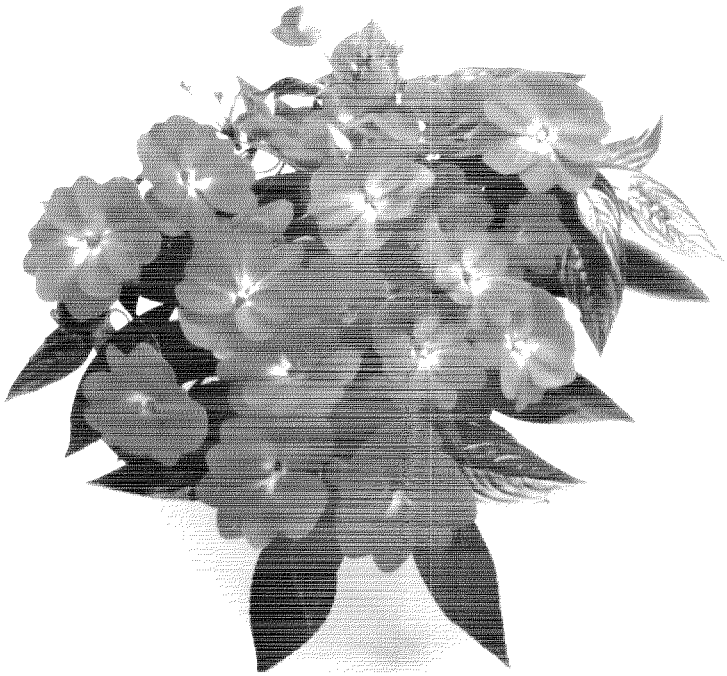
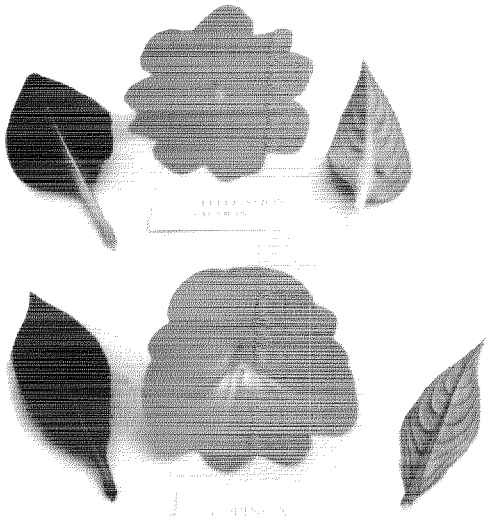

* * * * *